United States Patent [19]

Makiej

[11] Patent Number: 4,706,663

[45] Date of Patent: Nov. 17, 1987

[54] PARTICLE CATCHER FOR INHALATION DEVICES

[76] Inventor: Paul A. Makiej, 70 Mount Hope, Lowell, Mass. 01852

[21] Appl. No.: 856,047

[22] Filed: Apr. 25, 1986

[51] Int. Cl.[4] ............................................... B05B 1/26
[52] U.S. Cl. ........................... 128/200.18; 128/200.23; 128/205.27; 128/205.29
[58] Field of Search ...................... 128/200.18, 200.20, 128/203.15, 205.27, 205.29, 203.23; 272/99

[56] References Cited

U.S. PATENT DOCUMENTS

| | | | |
|---|---|---|---|
| 482,407 | 9/1892 | Magee | 128/203.15 |
| 1,696,469 | 12/1928 | Campbell | 128/203.15 |
| 1,839,193 | 1/1932 | Blanchard | 128/200.18 |
| 2,605,089 | 7/1952 | Dautrebande | 128/200.18 |
| 2,670,739 | 3/1954 | McNeill | 128/200.18 |
| 3,653,380 | 4/1972 | Hansen | 128/203.15 |
| 4,037,836 | 7/1977 | Puderbaugh et al. | 272/99 |
| 4,116,195 | 9/1978 | James | 128/203.15 |
| 4,116,387 | 9/1978 | Kremer, Jr. et al. | 128/200.18 |
| 4,353,365 | 10/1982 | Hattworth et al. | 128/203.15 |
| 4,484,577 | 11/1984 | Sackmer et al. | 128/203.29 |
| 4,570,630 | 2/1986 | Elliott et al. | 128/203.15 |

FOREIGN PATENT DOCUMENTS

| | | | |
|---|---|---|---|
| 305573 | 2/1933 | Italy | 128/200.18 |
| 6512222 | 4/1966 | Netherlands | 128/200.23 |
| 2110543 | 6/1983 | United Kingdom | 128/200.23 |

OTHER PUBLICATIONS

"Effects of Treatment with Beclomethasone Dipropionate in Subpopulations of Perennial Phinitis Patients", Peter Small, M.D., et al., reprinted from The Journal of Allergy and Clinical Immunology, St. Louis, vol. 70, No. 3, pp. 178-182, Sep. 1982.

"Aerosol Deposition Considerations in Inhalation Therapy", Stephen P. Newman, Ph.D., Recent Advances in Management of Obstructive Airways Disease, Chest/88/2/Aug. 1985/supplement, pp. 152S-160S.

"A Patient's Guide to Aerosol Therapy", Glaxo Inc., Ft. Lauderdale, FL 33309, Dec. 1981.

"Effects of Treatment with Beclomethasone Dipropionate in Subpopulations of Perennial Rhinitis Patients Efficacy and Safety of Vancenase TM Confirmed", Peter Small, M.D. et al., Montreal, Canada, copyright 1983, Schering Corporation.

New Aerochamber TM, Monaghan Medical Corporation, Plattsburgh, New York, HPC printed USA 10-84, lit. No. 74026.

New Brethancer TM Spacer-Inhaler, Geigy, 2/85.

Monaghan Aerochamber TM Aerosol Inhaler, Monaghan Medical Corporation, lit. P/N 74002 184.

Vancenase TM Nasal Inhaler, Schering Corporation, Kenilworth, N.J. 07033, copyright 1981, VCE-071/12400802 9.81.

Primary Examiner—Edward M. Coven
Assistant Examiner—J. P. Lacyk
Attorney, Agent, or Firm—Lorusso & Loud

[57] ABSTRACT

The present invention is a particle catcher for reducing the velocity of aerosol medications discharged from an inhalation device and the amount of large particle droplets entrained therein. A screen supportable with respect to the aerosol discharge of the inhalation device is integrally formed with, and along the cross section of, one end of a flexible support tube. The screen includes a structural array of interconnecting elements and openings which reduce the flow rate of the discharged spray and limit the size of particles and droplets in the spray which pass therethrough. The opposite end of the flexible tube is selectively moldable into the cross-sectional shape of the inhalation device mouthpiece.

8 Claims, 7 Drawing Figures

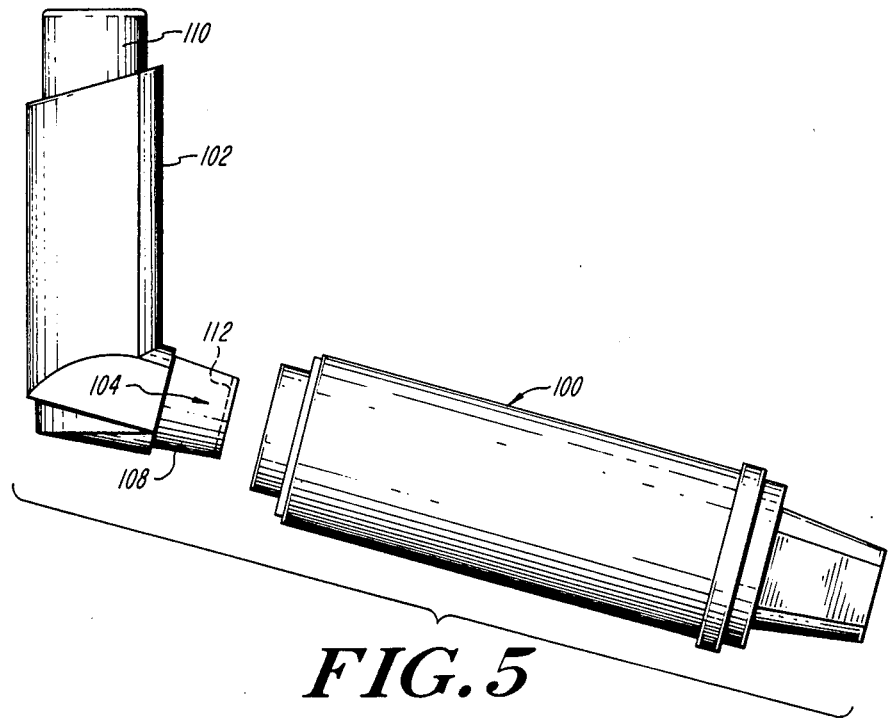
FIG. 5
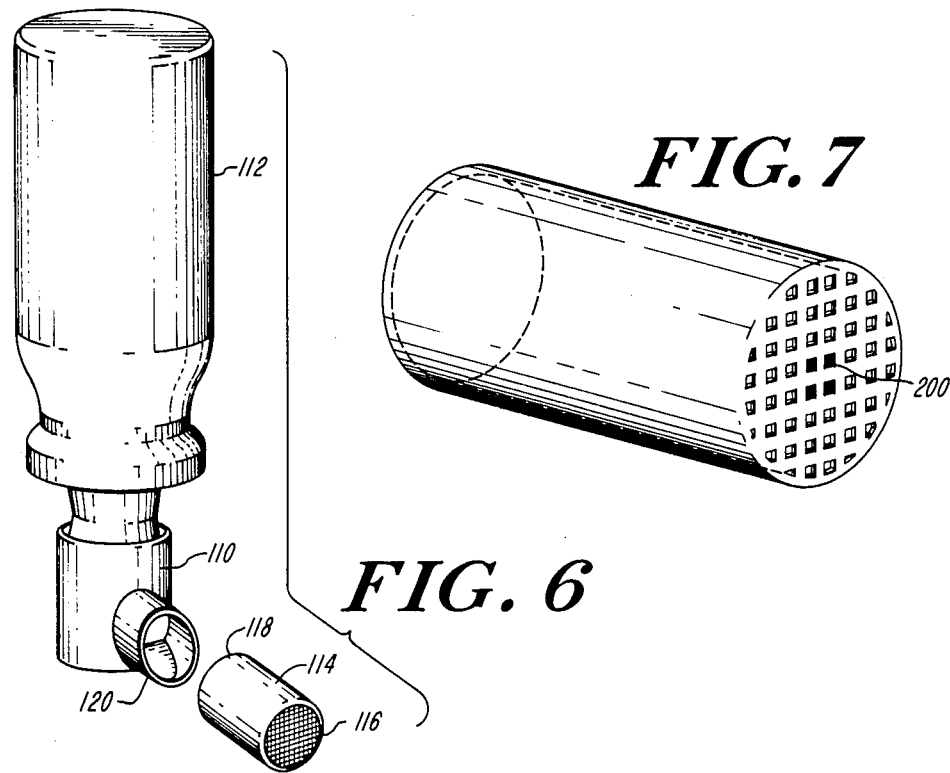
FIG. 7
FIG. 6

PARTICLE CATCHER FOR INHALATION DEVICES

FIELD OF INVENTION

The present invention relates to a device for improving the bronchial deposition of therapeutic aerosol medications and, more particularly, relates to a particle catcher for reducing the flow rate of aerosol medications discharged from an inhalation device and the number of large particles and droplets entrained therein.

BACKGROUND OF THE INVENTION

The use of inhalation devices to deliver carefully measured amounts of medication in order to dilute the bronchial passages is well known in the art. Inhalation therapy is preferred over oral and intravenous methods since a lesser amount of medication is required, the therapeutic effect occurs more rapidly, and there is a lower incidence of systemic side effects associated with use.

The first and foremost requirement of inhalation therapy is to ensure that a sufficient dose of medication reaches the lungs. Generally, the drug dose is deposited within the respiratory tract by a metered-dose inhaler. The metered-dose inhaler releases an aerosol spray consisting of large droplets of propellant within which the drug itself is encapsulated either as a powder or as a liquid. Since the drug particles and droplets are pressurized, their initial velocity upon discharge is extremely fast. Moreover, as a result of surface forces, the droplets and particles tend to cling together upon discharge so that large agglomerations form within the spray. Because the aerosol particles or droplets are large and the flow rate of the spray is rapid, most of the medication impacts in the oropharynx rather than in the bronchial passageways. Unfortunately, the sensation derived from oropharyngeal impaction may erroneously convince the patient that the required dose has been inhaled, when in reality the medication needed for bronchodilation has only been ingested. Consequently, the respiratory ailment remains untreated. The local impaction of the medication in the oropharynx can be especially deleterious when certain corticosteroid aerosols are utilized since local side effects such as oropharyngeal candidiasis or dysphonia may occur.

Deposition of the aerosolized medication in the lungs of the patient rather than his mouth would be more readily achieved if only the proper inhalation techniques were practiced. Several studies have shown, however, that a significant number of patients fail to either coordinate activation of the aerosol with inhalation, inhale slowly and deeply, or adequately breath-hold upon completion of inhalation. Consequently, a reduced amount of aerosol containing particles or droplets of medicine are deposited in the patient's lungs and, therefore, a reduced therapeutic effect results.

In order to ensure that a sufficient amount of the aerosolized drug deposits in the lungs of the user, even in patients with poor inhalation techniques, the prior art has developed several extension devices which attach directly to the metered dose inhalers. The extension devices provide an elongated chamber in which the propellant droplets can evaporate and large drug particles can settle so that only smaller and slower moving particles are ultimately inhaled by the patient. The reduced velocity and size of the particles allows the patient to slowly and deeply inhale the medication so that oropharyngeal impaction is reduced and bronchial deposition correspondingly increased.

Notwithstanding the increased lung deposition efficiency, however, other medically unrelated limitations arise when the extension devices are combined with metered-dose inhalers. The primary problem with extension devices is that they convey the image that the user is suffering from a serious medical illness. This false impression is derived from the fact that the majority of extension devices are bulky, cumbersome pieces of medical equipment, such as cylindrical chambers, multi-piece chambers, cone shaped spacers or collapsible bags, which range in length from 10 centimeters to 25 centimeters and in volume from 100 centimeters cubed to 1000 centimeters cubed. Because of their large size and awkward shape, extension devices cannot be easily carried on the person of the patient and, instead, must be lugged around by hand or in a carrying bag as unobtrusively as is possible. Moreover, problems often arise during inhalation of the large droplets sized medications which cause the patient to wheeze and cough, thereby drawing unwanted attention to his activities. Consequently, a patient may forego a scheduled treatment if the time of inhalation requires the use of the extension device in public in order to avoid the embarrasment of stigmatization frequently associated with illness in today's society. Although some collapsible extension devices are currently available which can be carried in a pocket or purse, these collapsible devices must stil be fully extended in order to allow the delivery of the desired medication. Hence, the prior art still lacks a small, portable metered-dose inhaler which is neither cumbersome nor large, yet which can effectively reduce the size and velocity of medicinal aerosols discharged therefrom.

SUMMARY OF THE INVENTION

The present invention is a particle catcher which reduces both the flow rate of aerosol drugs discharged from an inhalation device and the number of large particles and droplets entrained therein. In one important embodiment of the invention, the particle catcher comprises an injection molded plastic screen which is formed integral with, and along the cross section of, one end of a flexible support tube. The injection molded plastic screen is supportable with respect to the aerosol discharge of the inhalation device and includes a structural array of interconnecting elements and openings which reduce the flow rate of the discharged spray and limit the size of particles and droplets in the spray which pass therethrough. The opposite end of the flexible support tube is open and compressible into a variety of shapes which are coextensive with that of the inhalation device mouthpiece. During application, the open end of the support tube is slidably mounted around the end of the inhalation device communicating with the aerosol discharge, be it a mouthpiece or nasalpiece, so that the particle catching screen is positioned directly across the inhalation device mouthpiece or nasalpiece opening. Activation of the inhalation device's aerosol canister discharges a medicinal spray in the direction of the screen. The aerosolized medication communicates with the interconnecting elements and openings of the screen which reduce the velocity of the spray while preventing large particles and droplets from passing therethrough. Because the aerosolized drug which permeates the screen has a reduced velocity and particle size, oropharyngeal impaction is minimized and increased deposition in the desired bronchial passageways is achieved.

Accordingly, it is a primary object of the present invention to provide a particle catcher which reduces the size and velocity of aerosol droplets discharged from inhalation devices in order to reduce oropharyngeal impaction while increasing deposition of the aerosolized medicine in the desired bronchial passageways.

It is another object of the present invention to provide a particle catcher for an inhalation device which is small and unobtrusive.

It is another object of the present invention to provide a particle catcher which is universally adaptable to conventional metered-dose inhalers and extension devices.

It is another object of the present invention to provide a particle catcher which is simple and inexpensive to fabricate.

It is a still further object of the present invention to provide a particle catcher which provides less coordinated patients with the same comparable therapeutic benefits from their metered-dose inhalers as are achieved by patients with good inhalation skills.

BRIEF DESCRIPTION OF THE DRAWINGS

These and other details and advantages of the invention will be described in connection with the accompanying drawings in which:

FIG. 5 is a perspective view of an extension device attachable to a metered-dose inhaler which supports the particle catcher according to the preferred embodiment of the present invention;

FIG. 6 is a perspective view of an alternative embodiment of the particle catcher in which the particle catcher is supportable by a nasal inhaler; and FIG. 7 is a perspective view of the particle catcher according to an alternative embodiment of the invention in which a central region of the screen is sealed.

DESCRIPTION OF THE PREFERRED EMBODIMENT

At the outset, the invention is described in its broadest overall aspects with a more detailed description following. The present invention is a particle catcher for use in inhalation therapy which reduces the size and velocity of aerosol particles and droplets sprayed from an inhalation device so that an optimal amount of the dispensed medication is deposited in the respiratory tract of the patient rather than in the oropharynx or at bifurcations between the large central airways of the lungs. The therapeutic efficiency of aerosol therapy is primarily dependent upon ensuring that a sufficient amount of the inhaled drug reaches the lungs. Thus, it is imperative that the aerosol medium in which the drug is concentrated possesses the appropriate physical and kinetic characteristics necessary for optimal inhalation and communication with the patient's respiratory passageways. The particle catcher of the present invention accomplishes these important objectives both by preventing the majority of large droplets and agglomeration of droplets from leaving the inhalation device and by reducing the flow rate of the therapeutic spray which communicates with the patient's respiratory system. Slow and steady inhalation of the medication can therefore ensue, maximizing the quantity of the inhaled drug which penetrates to the peripheral parts of the patient's lungs.

Figure 1:
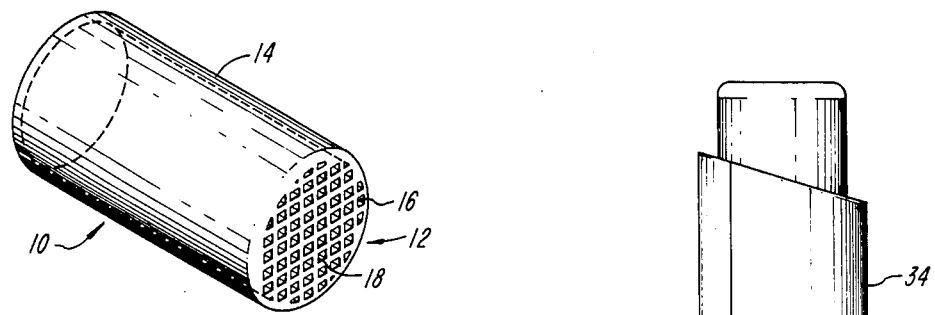
FIG. 1 is a perspective view of the particle catcher of the preferred embodiment of the invention.

In the preferred embodiment of the present invention illustrated in FIG. 1, the particle catcher 10 comprises a plastic screen 12 which is integrally formed with, and extends across the cross section of, one end of a flexible plastic support tube 14. The plastic screen preferably consists of an array of criss-cross interconnecting elements 16 which are separated at the interconnections by rectangular openings 18. Although in the preferred embodiment rectangular openings are used, other shaped openings such as circular, square, triangular or diamond can also be utilized, as is well known to those skilled in the art. The size of the screen opening is of particular sigificance since it controls the ability of the particle catcher to reduce both the aerosol droplet size and velocity. If the screen openings are too large, large aerosol droplets or agglomerations of droplets will pass from the inhaler and impact against the patient's oropharynx. Conversely, if the screen openings are too fine, none or few of the droplets will permeate the screen and bronchodialation of the patient's airways will be prevented. Of course, the size of the screen openings ultimately selected depends upon the drug and propellant selected, and for this reason an array of different size screen openings and shapes is encompassed by the present invention.

Ordinarily, the large droplets and agglomerations of droplets formed upon discharge from the inhalation device are dispersed uniformly through the spray medium. In some instances, however, the large droplets and agglomerations of droplets become entrained solely in the aerosol discharge which communicates with the screen center. Due to the high velocity and concentration of these droplets, the effectiveness of the particle catcher may become impaired. In order to compensate for the large percentage of droplets in the center of the medicinal spray, the openings in the center 200 of the particle catcher screen may be blocked off or sealed as shown in FIG. 7. This structural arrangement prevents the large droplets and agglomeration of droplets from leaving the inhalation device while allowing the finer sized droplets entrained in the periphery of the spray to pass through the outer screen openings which are not sealed. The sealing of the screen openings can be accomplished by either closing off the openings during the manufacturing process or by instead applying a shield or barrier across the openings subsequent to the fabrication of the particle catcher. In the latter embodiment, the screen shield may consist either of a coating of a medically safe resin or polymeric material or, instead, of a filter, cloth or other material which is supported along the screen openings relative to the area of large droplet concentration.

The width and length of the support tube 14 varies according to the width and length of the inhalation device mouthpiece upon which it will be mounted. The support tube need not be of coextensive geometric shape with that of the mouthpiece since its flexible nature allows it to assume varying embodiments under the appropriate stresses of use. The length of the support tube is dependent only upon assuring that the particle catcher is securely supported by the inhalation device. The flexibility of the support tube makes the particle catcher an extremely versatile device since it can be selectively molded by the user into a variety of shapes which easily slide around varyingly shaped inhalation device mouthpieces. The width of the support tube is preferably equivalent to, or slightly smaller than, the width of the mouthpiece upon which it is to be slidably mounted so that through the forces of resiliency the support tube compresses against the mouthpiece and is removably retained therein. Preferably, the support tube length is coextensive with the length of the mouthpiece so that the patient's hands, which usually grasp the mouthpiece at some point during inhalation, don't accidentally dislodge the particle catcher from the inhalation device during use. The support tube may also include fastening means such as an annular indentation which mates with an annular projection on the mouthpiece of the inhalation device, thereby providing a more secure engagement of the particle catcher to the inhalation device. Although such a fastening means enhances the stability of the connection of the particle catcher to the inhalation device, it also, however, requires that the inhalation device be fabricated with a male fastening means which is not currently the common practice in the art. On the other hand, additional fastening means are generally unnecessary since the inherent resilient forces possessed by the support tube are sufficient for ensuring the engagement of the particle catcher to the inhalation device under conditions of ordinary use.

The particle catcher of the preferred embodiment is preferably formed by an injection molding process so that a one piece, homogeneous particle catcher is produced having the screen integrally formed with, and extending across the cross section of, one end of the supporting tube. The particle catcher is preferably made from a chemical resistant plastic such as polypropylene or polyethylene based material. A flexible material such as a polyethylene-vinyl acetate plastic is particularly advantageous for fabricating the support tube since it ensures that the support tube can be slidably mounted upon, and supported by, a variety of geometrically shaped inhalation device mouthpieces. Alternatively, a more rigid plastic may be beneficial when the particle catcher is to be used with only one type of mouthpiece since a support tube possessing such a composition will retain its shape for a longer period of time and, therefore, other plastics besides polypropylene and polyethylene may be utilized, as is of course known to those skilled in the art.

Although in the preferred embodiment, the screen and support tube constitute a single plastic piece, in alternative embodiments the screen and support tube may constitute separate elements which can be fitted together and then mounted upon the mouthpiece of an inhalation device. In one such embodiment, one end of the support tube includes an annular retaining channel into which the screen is force fitted and peripherally locked. In another embodiment, the screen may be adhered to the support tube by the application of a resin or cement. The injection molded single piece particle catcher is preferred, however, since it provides a simple design, is capable of mass production and since it lacks any external projections such as dried resin or a retaining lip which could impede the flow of the drug through the rectangular openings located around the screen periphery.

Figure 2:
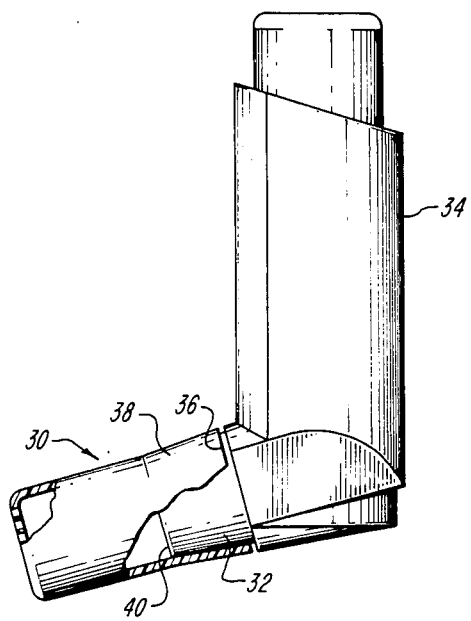
FIG. 2 is a perspective view, partly in section, of the preferred embodiment of the invention mounted upon the mouthpiece of an inhalation device.

Prior to the patient's receiving a dosage of the prescribed medication, the single piece homogeneous particle catcher 30 is mounted upon the mouthpiece 32 of the inhaler 34 as shown in FIG. 2. The open end 36 of the flexible support tube 38 opposite the screen end is manipulated into a shape somewhat commensurate with that of the mouthpiece cross section. The selectively molded open end 36 of the support tube 38 is mounted around the mouthpiece edge 40 and then slid axially along the mouthpiece 32 until the support tube 38 is securely, yet removably, mounted upon or supported by the inhalation device 34. The inherent resilient of the plastic support tube urges the walls of the support tube against the walls of the mouthpiece. The compression of the support tube walls against that of the mouthpieice ensures that the particle catcher 30 is fixedly maintained in position during the inhalation process. Although the support tube resilient forces operating against the mouthpiece are sufficient to support the particle catcher onto the inhalation device, they are, conversely, not so substantial as to prevent simple removal of the particle catcher by grasping and sliding the support tube in a reverse direction from that used in the mounting procedure. The ease in which the particle catcher can be removed from the inhalation device is particularly significant since the particle catcher must be removed periodically for cleansing to remove drug build up on the screen openings and thereby ensure its continual effectiveness as an aid in inhalation therapy.

The flexible nature of the support tube coupled with its inherent resiliency ensures that the mounting of the particle catcher onto the mouthpiece of the inhalation device is easily achieved. Of course, the inhalation device upon which the particle catcher may be mounted is not simply limited to a metered-dose inhaler but may also include other inhalation articles such as spacers, holding chambers, collapsible bags, or other extension devices. The particle catcher of the preferred embodiment is mounted upon the inhalation device's mouthpiece until the particle catching screen is positioned over the mouthpiece opening. Under this structural arrangement, the screen is supported by the inhalation device with respect to the aerosol discharged therefrom. The screen interconnecting elements and openings are particularly positioned so that they can intercept or impede the flow of large aerosol droplets and agglomeration of droplets when the aerosol canister received in the inhalation device is activated. Subsequent to activation of the aerosol canister 42, a metered-dose of medication is dispensed from the inhalation device spray valve in the direction of the mouthpiece. As the therapeutic aerosol medium communicates with the mouthpiece opening, it is intercepted by the particle catching screen and only those droplets and particles of medication finer than the screen openings pass from the inhalation device to the mouth and respiratory tract of the patient. Larger particles and agglomeration of particles are, conversely, caught in the interconnecting elements of the screen and are, therefore, prevented from being inhaled by the patient.

By slowing the flow rate of the aerosol's release from the inhalation device, the particle catcher allows the patient additional time to coordinate activation of the aerosol with slow and deep inhalation. At the same time, by introducing smaller droplets and particles at a reduced velocity into the respiratory tract, local impaction either in the oropharynx or at bifurcations between the large central airways of the lungs is minimized. The particle catcher therefore selectively removes large aerosol medication particles or droplets that ordinarily deposit in the mouth and throat while enabling finer droplets and particles to travel through the air passageways until they reach the lungs. Hence, by supporting the screen with respect to the aerosol discharge of the inhalation device, the desired therapeutic treatment can be effected while significantly reducing the amount of medication ingested by the patient.

Figure 3:
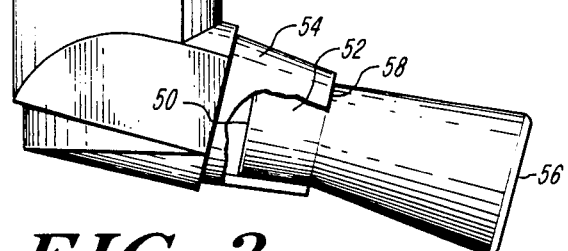
FIG. 3 is a perspective view, partly in section, of an alternative embodiment of the invention, in which the particle catcher is removably received within the inhalation device mouthpiece.

Although the particle catcher is preferably mounted upon the mouthpiece of the inhalation device, it may, alternatively, be removably received within the lateral extension of the mouthpiece communicating with the spray valve as illustrated in FIG. 3. In this embodiment, the open end 50 of the support tube 52 is thin walled, of slightly smaller diameter than the internal diameter of the mouthpiece 54 and of a similar cross sectional shape of that of the mouthpiece 54. The opposite end of the support tube in which the screen 56 is held is of a larger diameter than the open end 50. During application, the particle catcher is mounted within the mouthpiece extension by urging the support tube 52 into the mouthpiece opening 58 and along the mouthpiece extension until the mushroomed screen end 56 is sufficiently supported by the mouthpiece opening 54. The enlarged screen end 56 of the support tube not only aids in the engagement of the particle catcher to the inhalation device but also serves as a handle for facilitating the guiding and urging of the particle catcher into and out of the mouthpiece.

Figure 4:
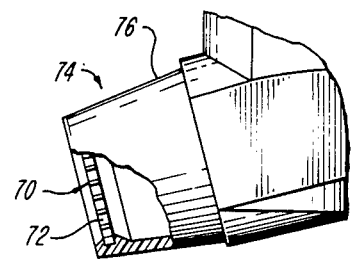
FIG. 4 is a perspective view, partly in section, of an alternative embodiment of the particle catcher in which the particle catching screen is supported by the internal periphery of the inhalation device mouthpiece.

In another alternative embodiment shown in FIG. 4, the particle catcher 70 consists simply of a screen 72 which is secured to the internal periphery of the inhalation device mouthpiece 74 or the extension 76 thereof. The screen 72 may be force fitted into the mouthpiece periphery or, more advantageously, may instead be retained in a channel in the mouthpiece interior wall. The particle catching screen 72 may have frayed ends as a consequence of simply being cut out of a larger mat or screen or may instead have bevelled or rounded edges which facilitate the insertion and retainment in the mouthpiece wall channel. Of course, the screen need not be force fitted into the mouthpiece interior but may, instead, be formed integral with the inhalation device mouthpiece. In such an embodiment, the screen preferably extends across the open end of the inhalation device mouthpiece. Of couse in this situation, the particle catcher is not separable from the inhalation device and, hence, the aerosol canister must be first removed from the inhalation device and then the whole device must be submerged in water in order to properly carry out the required periodic cleaning of the particle catcher screening.

The particle catcher's greatest influence on the therapeutic aerosol's flow rate and particle or droplet size occurs when it is positioned closely proximate to the spray valve such as when it is mounted upon, and supported by, a conventional metereddose inhaler. Nonetheless, the beneficial effects of the particles catcher also favor its use with spacers, settling chambers, collapsible bags and other extension devices which attempt to reduce the size and velocity of the aerosolized drugs through evaporation and gravitational settling. When utilizing the particle catcher with extension devices, the support tube is mounted upon the exension device mouthpiece by pressing the open end of the flexible support tube into a shape easily mountable over the mouthpiece and sliding the particle cather thereupon. To compensate for the beneficial effects of the particle and droplet settling, the screen openings of the particle catcher should be smaller than that utilized with the conventional metered-dose inhaler. As a result of the smaller screen openings, fine medication particles enter the patient's respiratory system thereby increasing the occurance of deposition of the medication in the far reaching areas of the lungs.

The most favorable combination of the particle catcher and the extension device arises when the extension device 100 is attached to a metered-dose inhaler 102 which already is disposed with a particle catcher 104 along the cross-sectional opening of the mouthpiece 108 as is shown in FIG. 5. When the aerosol canister 110 containing the medication is activated in such an embodiment, the ensuing therapeutic spray is injected against the particle screen 112 so that the majority of large droplets and agglomerations are prevented from passing into the extension device 100 and the flow rate of the spray is accordingly reduced. Consequently, a fine aerosolized medium is introduced into the extension device 100 which further separates the large droplets of particles from the smaller droplets and particles by gravitational settling and further reduces the velocity of the spray as a result of the increased width and length of the extension tract of the patient is therefore moving at a slow velocity and contains only substantially fine medication particles and droplets such that the slow, deep inhalation technique necessary for optimal therapeutic treatment may ensue. Of course, the same effect will result if the particle catching screen is supported by the extension device opening which receives the metered-dose inhaler rather than by the metered-dose inhaler itself. Alternatively, in order to reduce the velocity of the aerosol discharge and the number of large particles entrained therein, the particle catching screen could also be supported by the extension chamber between the metered-dose inhaler receiving end and the mouthpiece end.

In another alternative embodiment shown in FIG. 6, a particle catcher is utilized to reduce the flow rate of aerosol medications discharged from a nasal inhaler and the number of large particles and droplets entrained therein. In this embodiment, the open end 118 of the support tube is mounted upon the nasalpiece 120 which communicates with the discharge of the aerosol canister 112. During mounting, the open end is slid along the nasalpiece until it is securely, yet removably, supported thereon. In such an arrangement, the screen 116 is supported by the nasal inhaler with respect to the aerosol discharged therefrom. Subsequent to discharge, the aerosol medium communicates with the particle catching screen 116 and only those droplets and particles of medication finer than the screen openings pass from the nasal inhaler into the nasal passages. Larger particles and agglomerations of particles are, conversely, retained in the nasal inhaler by the interconnecting elements of the screen. Hence, by supporting the particle catcher 114 with respect to the discharge of the nasal inhaler, only those aerosolized drugs with a reduced velocity and particle size are deposited in the patient's nasal membranes and passageways and the desired therapeutic treatment can therefore be optimally effected.

It is to be understood that the preceding description is given merely by way of illustration and not in limitation of the invention and that various modifications may be made thereto without departing from the spirit of the invention as claimed.

What is claimed is:

1. A particle catcher for preventing particles, droplets and agglomerations of particles and droplets of a selected size in an aerosolized medicinal discharge of an inhalation device from passing from the inhalation device to the respiratory tract of a user, the inhalation device including a housing having a first end with an opening adapted to receive a canister containing a medicine that is dischargeable from the canister in an aerosolized form and a second end with a portion thereof defining an opening in communication with the outside, the housing also including means for discharging the medicine in aerosolized form from the canister towards the through the opening in the second end of the housing in communication with the outside, the particle catcher comprising:
    a hollow tube having an opening at a first end and an opening at a second end, said hollow tube having means for removably mounting said first end in a tight-fitting relationship with the housing so that said hollow tube and the opening in the second end of the housing are in fluid communication; and
    a screen having a plurality of apertures with each of said apertures being smaller in size than the particles, droplets and agglomeration of particles and droplets of a selected size, said screen being supported by said second end of said hollow tube across said opening at said second end;
    whereby when the aerosolized medicine is discharged from the inhalation device through the opening in the second end of the housing the aerosolized medicine passes through said hollow tube until the aerosolized medicine communicates with and passes through said screen with said screen preventing the particles, droplets and agglomerations of particles and droplets of a selected size from passing therethrough.

2. The particle catcher of claim 1 wherein the second end of the housing includes a main body and the portion of the second end of the housing defining the opening in communication with the outside extends from the main body and wherein said removably mountable means includes a first end of said hollow tube having an interior perimeter sufficient to mount said first end directly to the portion of the second end of the housing defining the opening in the housing in communication with the outside.

3. The particle catcher of claim 1 wherein said removably mountable means includes a first end of said hollow tube having an exterior perimeter sufficient to mount said first end within the opening in the second end of the housing in communication with the outside.

4. The particle of claim 1 wherein said first end of said hollow tube is flexible.

5. The particle catcher of claim 4 wherein the second end of the housing includes a main body and the portion of the second end of the housing defining the opening in communication with the outside extends from the main body and wherein said flexible first end of said holow tube is moldable into a shape having an interior perimeter sufficient to mount said first and directly to the portion of the second end of the housing defining the opening in the housing in communication with the outside.

6. The particle catcher of claim 1 wherein said screen further includes means for sealing said apertures at a central region of said screen. particles and droplets of agglomerations of particles and droplets are prevented by said sealing means from passing through said .

7. The particle catcher of claim 1 wherein said screen is formed integral with said hollow tube that said screen and said hollow tube comprise a single piece.

8. A particle catcher for preventing particles, droplets and agglomerations of particles and droplets of a selected size in an aerosolized medicinal discharge of an inhalation device from passing from the inhalation device to the respiratory tract of a user, the inhalation device including a housing having a first end with an opening adapted to receive a canister containing a medicine that is dischargeable from the canister in an aerosolized form and a second end with a portion thereof defining an opening in communication with the outside, the housing also including means for discharging the medicine in aerosolized form from the canister towards and through the opening in the second end of the housing in communication with the outside, the particle catcher comprising:
    a hollow tube having an opening at a first end and an opening at a second end, said hollow tube having means for removably mounting said first end in a tight-fitting relationship with the housing so that said hollow tube and the opening in the second end of the housing are in fluid communication; and
    a screen having a plurality of apertures with each of said apertures being smaller in size than the particles, droplets and agglomeration of particles and droplets of a selected size, said screen being supported by said tube in a cross-sectional plane through said tube;
    whereby when the aerosolized medicine is discharged from the inhalation device through the opening in the second end of the housing the aerosolized medicine passes through said hollow tube until the aerosolized medicine communicates with the passes through said screen with said screen preventing the particles, droplets and agglomerations of particles and droplets of a selected size from passing therethrough.

* * * * *

UNITED STATES PATENT AND TRADEMARK OFFICE
CERTIFICATE OF CORRECTION

PATENT NO. : 4,706,663
DATED : November 17, 1987
INVENTOR(S) : Paul A. Makiej

It is certified that error appears in the above—identified patent and that said Letters Patent is hereby corrected as shown below:

Col. 1, line 15, change "dilute" to --dilate--;
Col. 2, line 21, change "droplets" to --droplet--;
Col. 6, line 16, change "resilient" to --resiliency--;
Col. 8, line 31, after "extension" insert --chamber 100. The drug dose which ultimately reached the respiratory--;

--and--;
Claim 5, Col. 10, line 7, change "holow" to --hollow--;
Col. 10, line 9, change "and" to --end--;
Claim 6, Col. 10, lines 15-17, after "." delete "particles" and droplets of agglomerations of particles and droplets are prevented by said sealing means from passing through said";
Claim 7, Col. 10, line 19, after "tube" insert --such--:

Signed and Sealed this

Thirty-first Day of May, 1988

Attest:

DONALD J. QUIGG

Attesting Officer

Commissioner of Patents and Trademarks